United States Patent
Mullaney

(10) Patent No.: US 12,232,772 B2
(45) Date of Patent: Feb. 25, 2025

(54) STRUT ASSEMBLIES AND EXTERNAL FIXATION SYSTEMS

(71) Applicant: ARTHREX, INC., Naples, FL (US)

(72) Inventor: Michael W. Mullaney, Naples, FL (US)

(73) Assignee: ARTHREX, INC., Naples, FL (US)

( * ) Notice: Subject to any disclaimer, the term of this patent is extended or adjusted under 35 U.S.C. 154(b) by 456 days.

(21) Appl. No.: 17/576,065

(22) Filed: Jan. 14, 2022

(65) Prior Publication Data

US 2022/0133357 A1 May 5, 2022

Related U.S. Application Data

(63) Continuation of application No. PCT/US2020/041922, filed on Jul. 14, 2020.

(60) Provisional application No. 62/874,104, filed on Jul. 15, 2019.

(51) Int. Cl.
*A61B 17/60* (2006.01)
*A61B 17/62* (2006.01)
*A61B 17/64* (2006.01)
*A61B 17/00* (2006.01)

(52) U.S. Cl.
CPC .......... *A61B 17/6425* (2013.01); *A61B 17/62* (2013.01); *A61B 2017/00991* (2013.01); *A61B 2017/606* (2013.01)

(58) Field of Classification Search
CPC ......... A61B 17/60; A61B 17/62; A61B 17/64; A61B 17/6475
See application file for complete search history.

(56) References Cited

U.S. PATENT DOCUMENTS

2008/0269741 A1\* 10/2008 Karidis ................. A61B 17/62
606/56
2009/0198234 A1 8/2009 Knuchel
(Continued)

OTHER PUBLICATIONS

International Search Report and Written Opinion of the International Searching Authority for PCT/US2020/041922, Sep. 25, 2020, 8 pages.

(Continued)

*Primary Examiner* — Eduardo C Robert
*Assistant Examiner* — Michelle C Green
(74) *Attorney, Agent, or Firm* — Carlson, Gaskey & Olds, P.C.

(57) ABSTRACT

Length-adjustable strut assemblies and external fixation systems utilizing such strut assemblies are disclosed. A strut assembly comprises an externally threaded rod portion including a first externally threaded rod member, and a strut barrel assembly including a strut barrel portion with an internal cavity and an adjustment portion, the rod portion extending within the internal cavity of the strut barrel portion and selectively threadably coupled with at least one key of the adjustment portion. The strut assembly further comprises a first joint assembly at an end of the first externally threaded rod member and a second joint assembly at an end of the strut barrel portion. At least one portion of the second joint is configured to be selectively disassembled from the end of the strut barrel portion to expose the internal cavity of the strut barrel portion and the second end of the rod portion.

26 Claims, 16 Drawing Sheets

(56) References Cited

U.S. PATENT DOCUMENTS

| | | | |
|---|---|---|---|
| 2011/0208187 A1* | 8/2011 | Wong | ................ A61B 17/6416 |
| | | | 606/56 |
| 2012/0303028 A1 | 11/2012 | Wong | |
| 2014/0276817 A1* | 9/2014 | Murray | ................ A61B 17/62 |
| | | | 606/56 |
| 2016/0022314 A1 | 1/2016 | Bordeaux et al. | |
| 2017/0150994 A9 | 6/2017 | Cresina et al. | |
| 2018/0268888 A1* | 9/2018 | Ohsawa | ................ G11C 11/161 |
| 2018/0344354 A1 | 12/2018 | Mullaney | |
| 2019/0125407 A1 | 5/2019 | Lauf | |

OTHER PUBLICATIONS

International Preliminary Report on Patentability for International Application No. PCT/US2020/041922 Jan. 18, 2022, 6 pages, International Bureau of WIPO.

* cited by examiner

STRUT ASSEMBLIES AND EXTERNAL FIXATION SYSTEMS

CROSS REFERENCE TO RELATED APPLICATION

This application claims priority benefit of and is a continuation of PCT International Application No. PCT/US2020/041922 filed on Jul. 14, 2020, and entitled Strut Assemblies and External Fixation Systems, which claims priority benefit under 35 U.S.C. § 119(e) of U.S. Provisional Application No. 62/874,104 filed on Jul. 15, 2019, and entitled External Fixation Systems and Strut Assemblies Thereof, which are incorporated herein by reference in their entireties.

FIELD OF THE DISCLOSURE

The present disclosure is generally directed to external fixation systems and related methods. More particularly, the present disclosure is directed to length-adjustable strut assemblies for external bone fixation systems and related methods that couple between a pair of platforms configured to affix to bone/anatomical segments.

BACKGROUND

External fixation devices have been used to treat bone and tissue conditions by positioning bone or tissue segments in desired relative positions based on particular clinical needs. One form of external fixation devices is a hexapod fixation device. Hexapod devices, or more formally called Stewart platforms, include six degree of freedom (6DOF) parallel manipulators or struts. Generally, these devices have the ability to manipulate an article of interest relative to a base in all three orthogonal axis translations (X, Y, Z position) and all rotations about those three orthogonal axes (roll, pitch, yaw and pose).

When configured as bone or tissue fixation systems, hexapod systems typically include a pair of rings that serve as bone fixation platforms. The platforms are typically connected with six struts that extend between the platforms. The struts and platforms are commonly connected via spherical or cardan joints that allow three rotations about three orthogonal axes. While some of these struts allow for length adjustment, their minimum and/or maximum lengths may not meet the needs of a particular clinical situation. For example, minimizing the distance between the platforms to a distance less than that afforded by a particular strut requires the use of a shorter struts—which naturally limits the adjustable range (i.e., the maximum length) of the struts.

As a result, current hexapod bone fixation systems utilize a collection of struts of differing lengths (or differing length ranges) which provide "short" struts for use when the platforms need to be close together and "long" struts for use when the platforms need to be further apart. In many instances these struts must be progressively or regressively swapped for the next length strut during a bone or tissue correction process, which is both a time consuming and costly process given that the strut being replaced cannot be re-used. Further complicating such systems is that some situations require a variety of differing strut lengths. For example, a variety of differing strut lengths is commonly required when extreme initial angulations or rotations are present. The selection process of the correct combination of differing strut lengths in such a situation is a time consuming process that is typically carried out by trial and error in an operating room. Such systems and situations thereby also require an excessive amount of inventory, which is also costly and often confusing to properly utilize.

Physically changing struts, aside from being a nuisance, also limits the available dynamic range of the system when attempting to reduce a deformity in an acute fashion. In this situation, struts are usually not added until such an acute correction is accomplished leaving the reduction to be held by operation room staff while additional members of the operation room staff pick and choose which struts will fit between the platforms at the prescribed locations. This process is time consuming and requires a large inventory.

Current hexapod fixation systems also typically utilize connections between the platforms and struts that require the use of one or more fasteners that need be tightened at the time of application. As such, connecting six struts at both ends to the platforms (i.e., twelve connections), sometimes in a trial and error fashion, is a difficult and time consuming task. Complicating matters is the fact that many current hexapod fixation systems utilize loose fasteners which must be applied using instruments. These fasteners and instruments add to the collection of parts and materials which must be kept track of in an operating room setting while the fixation system is employed, such as while a reduction is trying to be maintained.

Accordingly, hexapod fixation systems and related methods that provide increased length adjustment ranges while remaining coupled to the platforms, decrease the amount of associated inventory, can be installed relatively quickly, and reduce costs are desirable.

SUMMARY

In one aspect, the present disclosure provides external bone fixation system, comprising a first platform, a second platform, and at least one length-adjustable strut assembly. The first and second platforms each define an opening and configured to couple to an anatomical structure. The at least one length-adjustable strut assembly comprises an externally threaded rod portion including at least a first threaded rod member, and a strut barrel assembly including a strut barrel portion with an internal cavity and an adjustment portion, the rod portion extending within the internal cavity of the strut barrel portion and threadably coupled with at least one key of the adjustment portion. The at least one length-adjustable strut assembly further comprises a first joint assembly removably coupling a first end of the first threaded rod member with the first platform, the first joint assembly allowing angulation and rotation between the first threaded rod member and the first platform. The at least one length-adjustable strut assembly also comprises a second joint assembly removably coupling an end of the strut barrel portion with the second platform, the second joint assembly allowing angulation and rotation between the strut barrel assembly and the second platform. At least one portion of the second joint is configured to be selectively disassembled from the end of the strut barrel portion to expose the internal cavity of the strut barrel portion and the second end of the rod portion.

In some embodiments, selective rotation of the adjustment portion and/or the strut barrel portion rotates the at least one key about the rod portion and thereby adjusts an axial length of the strut assembly between the first and second platforms.

In some embodiments, the external bone fixation system further comprises a second threaded rod member and an externally threaded connecting element, the second threaded rod member and the first threaded rod member being internally threaded and configured to threadably mate with a corresponding portion of the external threads of the connecting element to couple the first and second threaded rod members together when the internal cavity of the strut barrel portion and the second end of the rod portion are exposed. In some such embodiments, a first portion of the external threads of the connecting element and the internal threads of the first threaded rod comprise a first pitch, and a second portion of the external threads of the connecting element and the internal threads of the second threaded rod comprise a second pitch that differs from the first pitch.

In some embodiments, the second joint assembly comprises a universal joint. In some such embodiments, the universal joint comprises a first yoke portion configured to be coupled to the first platform, a second yoke portion at the end of the strut barrel portion, and cross assembly rotatably coupled with the first and second yoke portions. In some such embodiments, the cross assembly is configured to be selectively disassembled from the second yoke portion.

In another aspect, the present disclosure provides a length-adjustable strut system. The system comprises an externally threaded rod portion including a first threaded rod member, and a strut barrel assembly including a strut barrel portion with an internal cavity and an adjustment portion, the rod portion extending within the internal cavity of the strut barrel portion and threadably coupled with at least one key of the adjustment portion. The system further comprises a first joint assembly at a first end of the first threaded rod member, the first joint assembly configured to removably couple to a first platform and allow angulation and rotation between the first threaded rod member and the first platform. The system also comprises a second joint assembly at an end of the strut barrel portion, the second joint assembly configured to removably couple to a second platform and allow angulation and rotation between the strut barrel assembly and the second platform. At least one portion of the second joint is configured to be selectively disassembled from the end of the strut barrel portion to expose the internal cavity of the strut barrel portion and the second end of the rod portion.

In some embodiments, selective rotation of the adjustment portion and/or the strut barrel portion rotates the at least one key about the rod portion and thereby adjusts an axial length of the strut assembly between the first and second joints.

In some embodiments, the system further comprises a second threaded rod member and an externally threaded connecting element, the second threaded rod member and the first threaded rod member being internally threaded and configured to threadably mate with a corresponding portion of the external threads of the connecting element to effectuate coupling of the first and second threaded rod members together when the internal cavity of the strut barrel portion and the second end of the rod portion are exposed. In some such embodiments, a first portion of the external threads of the connecting element and the internal threads of the first threaded rod comprise a first pitch, and a second portion of the external threads of the connecting element and the internal threads of the second threaded rod comprise a second pitch that differs from the first pitch.

In some embodiments, the second joint assembly comprises a universal joint. In some such embodiments, the universal joint comprises a first yoke portion configured to be couple to the first platform, a second yoke portion at the end of the strut barrel portion, and cross assembly rotatably coupled with the first and second yoke portions. In some such embodiments, the cross assembly is configured to be selectively disassembled from the second yoke portion.

In another aspect, the present disclosure provides a length-adjustable strut assembly comprising: an externally threaded rod portion including a first externally threaded rod member; a strut barrel assembly including a strut barrel portion with an internal cavity and an adjustment portion, the rod portion extending within the internal cavity of the strut barrel portion and selectively threadably coupled with at least one key of the adjustment portion; a first joint assembly at an end of the first externally threaded rod member, the first joint assembly configured to removably couple to a first platform and allow angulation and rotation between the first externally threaded rod member and the first platform; and a second joint assembly at an end of the strut barrel portion, the second joint assembly configured to removably couple to a second platform and allow angulation and rotation between the strut barrel assembly and the second platform. At least one portion of the second joint is configured to be selectively disassembled from the end of the strut barrel portion to expose the internal cavity of the strut barrel portion and an end of the rod portion.

In some embodiments, the second joint assembly comprises a universal joint. In some such embodiments, the universal joint comprises a first yoke portion configured to be couple to the first platform, a second yoke portion at the end of the strut barrel portion, and cross assembly rotatably coupled with the first and second yoke portions. In some such embodiments, the cross assembly is configured to be selectively disassembled from the second yoke portion. In such some embodiments, the cross assembly is coupled to the second yoke portion via a first removable pin portion of the cross assembly. In some such embodiments, the first removable pin portion extends between a pair of spaced arm portions of the second yoke portion and is coupled to a second pin portion of the cross assembly. In some such embodiments, the second pin portion extends between a pair of spaced arm portions of the first yoke portion. In some such embodiments, the first removable pin portion and the second pin portion are coupled together via a universal joint block. In some such embodiments, the first removable pin portion comprises a pin extending through a through hole of the universal joint block. In some such embodiments, the second pin portion comprises a pair of pin members extending within a pair of corresponding apertures of the universal joint block.

In some embodiments, the end of the rod portion includes an internally threaded internal axial aperture.

In some embodiments, the rod portion includes a second externally threaded rod member coaxially coupled to an end portion of the first externally threaded rod member. In some such embodiments, the first externally threaded rod member and the first externally threaded rod member include external threads that form a continuous external thread profile. In some such embodiments, the first externally threaded rod member and the first externally threaded rod member are coupled via a connecting member, and a first portion of the connecting member is threadably coupled within a first internally threaded internal axial aperture of the first externally threaded rod member and a second portion of the connecting member is threadably coupled within a second internally threaded internal axial aperture of the second externally threaded rod member. In some such embodiments, the first portion of the connecting member and the first internally threaded internal axial aperture of the first externally threaded rod member include threads of a first pitch, and the second portion of the connecting member and the second internally threaded internal axial aperture of the second externally threaded rod member include threads of a second pitch that differs from the first pitch.

In some embodiments, selective rotation of the adjustment portion and/or the strut barrel portion rotates the at least one key about the rod portion and thereby adjusts an axial length of the strut assembly between the first and second joints. In some embodiments, selective rotation of the adjustment portion rotates the strut barrel portion, and rotation of the strut barrel portion rotates the at least one key about the rod portion and thereby adjusts an axial length of the strut assembly between the first and second joints.

In some embodiments, the adjustment portion further comprises a sleeve member movable coupled over an end collar portion of the strut barrel portion and at least one pin member extending through a corresponding aperture in the end collar portion. In some such embodiments, a first end portion of the at least one pin member engages a back side of the at least one key and a second end portion of the at least one pin member engages an interior surface of the sleeve member. In some further such embodiments, the back side of the at least one key includes a depression, the second end portion of the at least one pin member being positioned within the depression. In some further such embodiments, the interior surface of the sleeve member includes at least one first portion configured as a cam surface that radially positions the at least one pin member such that the at least one pin member positions the at least one key in threaded engagement with the externally threaded rod portion. In some such embodiments, when the at least one pin member is engaged with the at least one first portion of the interior surface of the sleeve member, the rotation of the sleeve member effectuates rotation of the at least one pin member, the at least one key and the strut barrel portion. In some further such embodiments, the interior surface of the sleeve member includes at least one second portion configured as a relief surface that radially positions the at least one pin member such that the at least one pin member positions the at least one key such that the at least one key is threadably decoupled from the externally threaded rod portion. In some such embodiments, the adjustment portion further comprises at least one biasing member that naturally biases the at least one key radially away from the externally threaded rod portion. In some further such embodiments, the at least one first portion and the at least one second portion of the interior surface of the sleeve member are axially and/or angularly spaced. In some such embodiments, the adjustment portion further comprises at least one spring member that biases the sleeve member in an axial and/or angular arrangement with respect to the strut barrel portion such that the sleeve member is normally biases into a position with the at least one pin member engaged with the at least one first portion of the interior surface of the sleeve member.

In another aspect, the present disclosure provides an external bone fixation system, comprising: a first platform defining an opening and configured to couple to a first anatomical structure; a second platform defining an opening and configured to couple to a second anatomical structure; and at least one length-adjustable strut assembly comprising any of the strut assemblies disclosed above.

In some embodiments the first joint assembly is removably coupled with the first platform, and the second joint assembly is removably coupled with the second platform.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the external bone fixation systems and related methods described herein there is shown illustrative embodiments. These illustrative embodiments are in no way limiting in terms of the precise arrangement and operation of the disclosed external fixation systems and other similar embodiments are envisioned.

DETAILED DESCRIPTION

Figure 1:
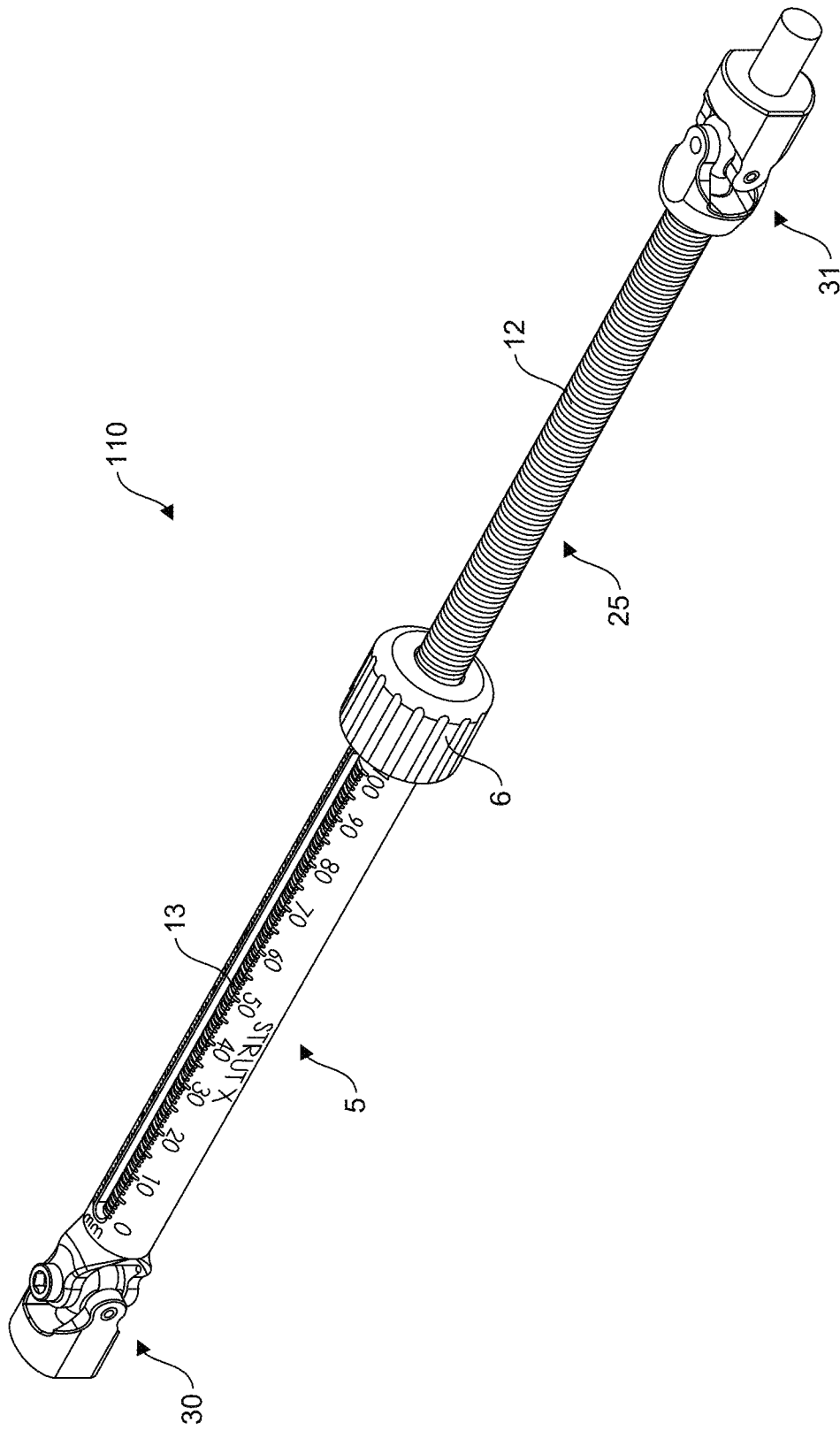
FIG. 1 illustrates an elevational perspective view of a strut assembly for an external bone fixation system.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure provides for six degree of freedom (6DOF) bone or tissue fixation systems and related fixation methods which include the desirable stability and mobility characteristics of a hexapod system without time consuming strut-length choices and assembly difficulties. The fixation systems include struts assemblies 110 with relatively large dynamic ranges such that acute reductions in the operating room are not limited by the system itself and the necessity of selecting and replacing one or more of the struts 110 during the reduction process. In some embodiments, the fixation systems, struts assemblies 110 and related fixation methods of the present disclosure are particularly advantageous for the repair of fractures or deformities, such as fractures of or deformities in relatively long bones.

The strut assemblies 110 and/or components thereof may be similar or the same as the strut assemblies disclosed in U.S. Patent Publication No. 2018/0344354, which is hereby incorporated herein by reference in its entirety. Further, while a single struts assembly 110 is shown in the figures, a fixation system and related fixation method according to the present disclosure will include several of the single struts assemblies 110 moveably coupled to and extending between a pair of platforms, as disclosed in U.S. Patent Publication No. 2018/0344354.

As shown in FIGS. 1-9C, in one embodiment, the fixation systems or devices include strut assemblies 110 each formed of a threaded rod assembly 25 threadably coupled within a strut body 5. As explained further below, the threaded rod assembly 25 may include a first strut screw or rod 12 and, potentially, a second add-on strut screw or rod 13. The threaded rod assembly 25 may include external threads, as shown in FIGS. 1-9C. As shown FIG. 3, the threaded rod assembly 25 may include or define a longitudinal axis X-X, and may be elongate along the axis X-X. In some embodiments, the threaded rod assembly 25 may be cylindrical.

As shown in FIGS. 1-9C, the threaded rod assembly 25 may be translatably received within the strut body 5. The strut body 5 may thereby include a non-threaded and potentially substantially smooth cavity configured to accept the threaded rod assembly 25 therein/therethrough, such as along the longitudinal axis X-X. The strut body 5, and potentially the cavity thereof, may define a length along the longitudinal axis X-X that is less than the length of the threaded rod assembly 25, as shown in FIGS. 1-9C. The strut body 5 may be configured such that the threaded rod assembly 25 is free to extend and/or translate through the strut body 5.

Figure 10:
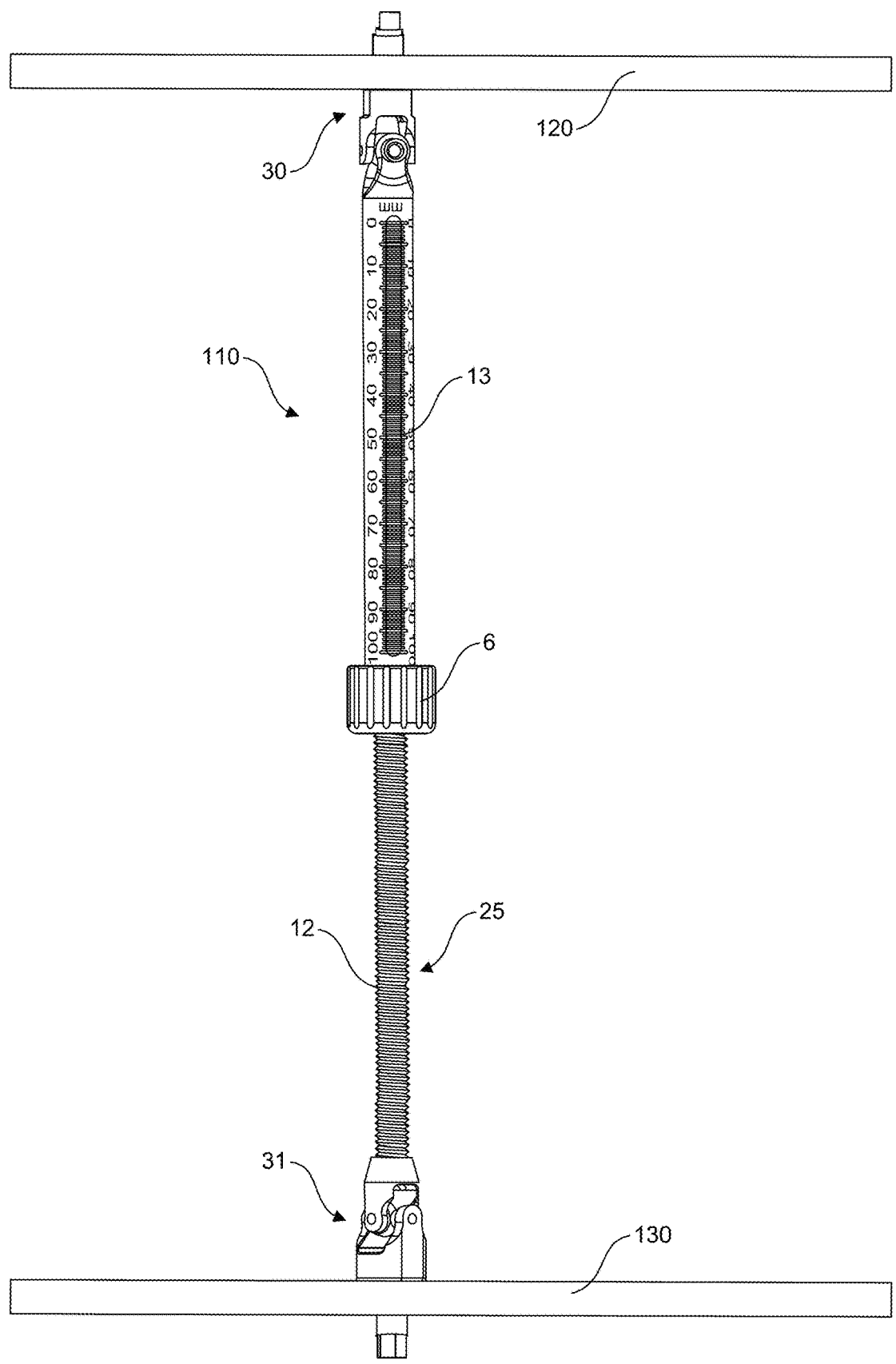
FIG. 10 illustrates a side view of the strut assembly of FIGS. 1-9C coupled between a pair of external bone fixation platforms.

As explained further below, a joint at one end of the strut body 5 is configured to be coupled to a first platform 120, and an opposing end of the threaded rod assembly 25 is configured to be coupled to a second platform 130, as shown in FIG. 10. In this way, the strut body 5 and the threaded rod assembly 25 may translate with respect to each other along the axis X-X to provide a relatively large range of length adjustability to the strut assembly 110 and, thereby the distance and/or orientation between the first and second platforms 120, 130.

The first and/or second platforms 120, 130 may be rings or partial rings such that they extend, at least partially, about an opening and/or an axis (and, potentially, at least partially about bone and/or tissue in situ). The strut assembly 110 may be coupled to the first and second platforms 120, 130 about the axis thereof. For example, a plurality of the strut assemblies 110 may be positioned and coupled circumferentially to the first and second platforms 120, 130, and each strut assembly 110 may be attached to the first and second platforms 120, 130 at differing positions about the axis of the platforms 120, 130. As such, the strut assemblies 110 may be angled with respect to the axis of the platforms 120, 130.

The strut assemblies 110 may be arranged and coupled with the first and second platforms 120, 130 in such a configuration that provides clearance for the extension of the threaded rod assembly 25 from the strut body 5 (or vice versa). For example, the strut assemblies 110 may be coupled to the first and second platforms 120, 130 in pairs of adjacent and relatively closely spaced joints, and such pairs of strut assemblies 110 may be spaced a relatively closely greater distance apart about the first and second platforms 120, 130. The strut assemblies 110 may thereby joined to the first and second platforms 120, 130 in an alternating pattern or orientation. However, in some other embodiments, the strut assemblies 110 may extend between the first and second platforms 120, 130 in the same directions or orientations.

Figure 9A:
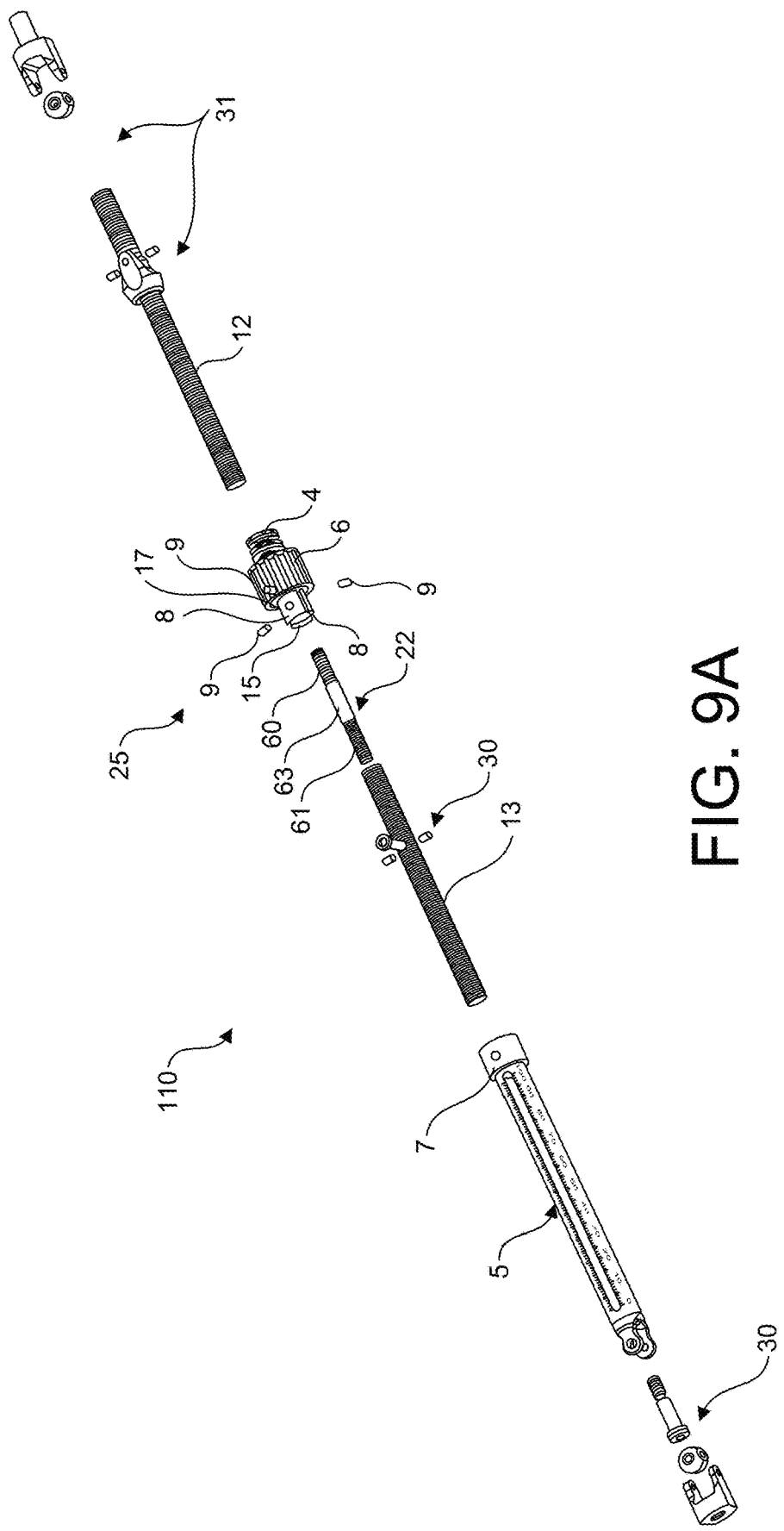
FIG. 9A illustrates an exploded elevational perspective view of the strut assembly of FIG. 1.
Figure 9B:
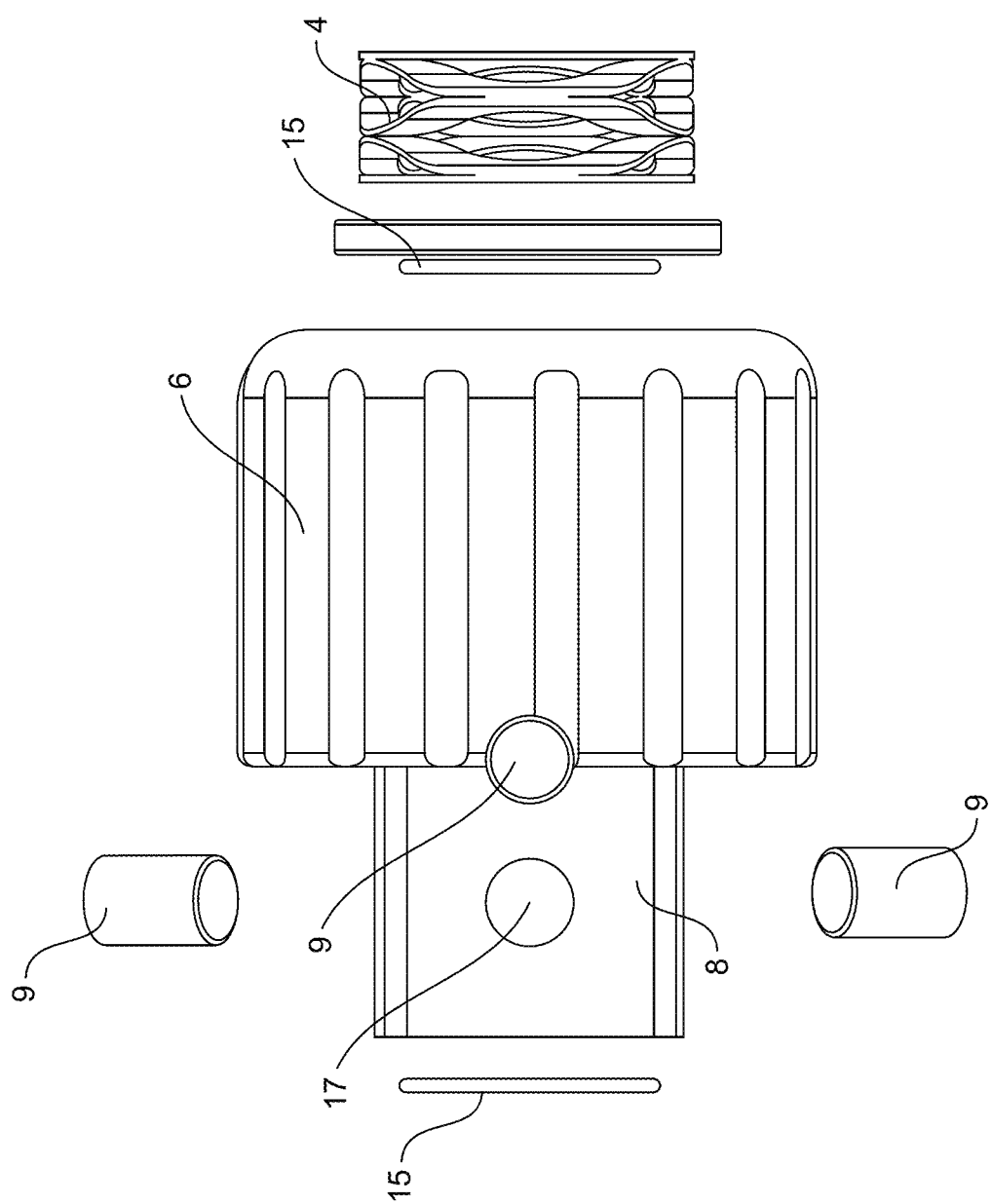
FIG. 9B illustrates an exploded side view of a length adjustment mechanism of the strut assembly of FIG. 1.
Figure 9C:
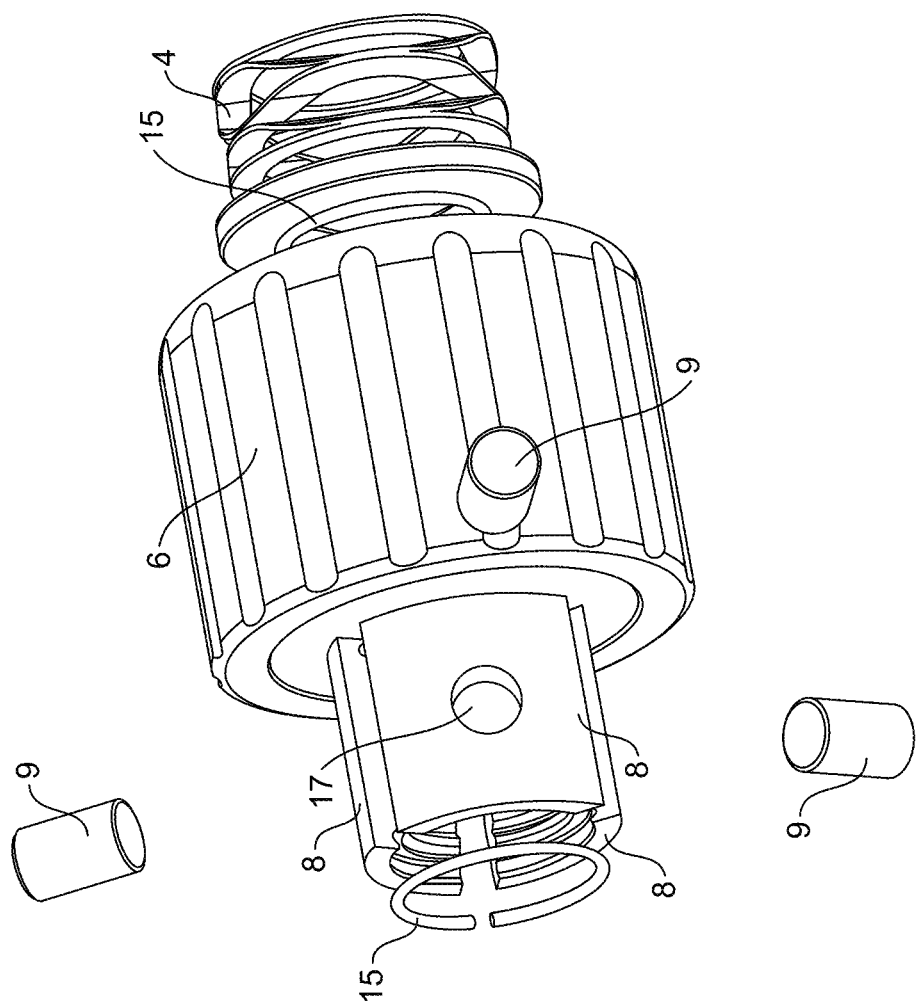
FIG. 9C illustrates an exploded elevational perspective view of the length adjustment mechanism of FIG. 1.

As shown in FIGS. 1-9C and described above, the threaded rod assembly 25 (comprising the first strut screw or rod 12 and, potentially, the second add-on strut screw or rod 13) may be provided within the open cavity of the strut body 5 and threadably engage with corresponding internal threads of a length adjustment mechanism of the threaded rod assembly 25. In some embodiments, the strut body 5 of the strut assemblies 110 may be threadably engaged with the threaded rod assembly 25 via at least one threaded key 8 of the length adjustment mechanism, as shown in FIGS. 9A-9C. The at least one key 8 may include or form internal thread that correspond to/engage with the external thread of the threaded rod assembly 25. The strut assemblies 110 may be configured such that the at least one key 8 (such as two, three or more keys 8) is able to be manually moved radially (i.e., translated in and out in a radial fashion with respect to the axis X-X) to engage and disengage the threaded rod assembly 25.

As shown in FIGS. 1-9C, at least one threaded key 8 may be provided within an inner opening/cavity within an end collar portion 7 of the strut body 5, and the actuation of the at least one threaded key 8 may be accomplished via rotation (e.g., manual rotation, potentially about the axis X-X) and/or longitudinal translation (e.g., manual translation, potentially along the axis X-X) of an outer sleeve or ring 6. The outer sleeve 6 may be rotatably and/or translatably provided on/about the end collar portion 7, as show in FIGS. 1-9C. As shown in FIGS. 9A-9C, at least one pin 9 may radially extend through the collar portion 7 (e.g., through a corresponding through-hole or aperture) and bear against a back/inside surface of the at least one threaded key 8. The back/inside surface of the at least one threaded key 8 may include an aperture, cavity or depression 17 in which the at least one at least one pin 9 is positioned and bears against, as shown in FIGS. 9A-9C.

The outer sleeve 6 may include an inner camming surface such that when the sleeve 6 is longitudally/axially translated (e.g., along the axis X-X) and/or rotated (e.g., about the axis X-X), the camming surface either allows the at least one pin 9 and the at least one threaded key 8 to move radially outward away from and out of engagement with the threaded rod assembly 25 or forces the at least one pin 9 radially inward to in turn force the at least one threaded key 8 radially inwards and into engagement with the threaded rod assembly 25 (i.e., the first strut screw 12 and/or the second add-on strut screw 13). The outer sleeve 6 may also be configured such that rotation of the outer sleeve 6 about the axis X-X when the at least one threaded key 8 is forced into engagement with the threaded rod assembly 25 via the camming surface of the outer sleeve 6 causes rotation of the at least one threaded key 8 about the threaded rod assembly 25 such that the threaded rod assembly 25 is axially translated through the strut body 5 (the axial direction (i.e., lengthening or shortening of the strut assembly 110) depending upon the direction of the rotation of the outer sleeve 6). For example, the outer sleeve 6 may be configure such that rotation thereof acts against the at least one pin 9, which in turn acts against the collar portion 7 (via the aperture thereof) and the at least one threaded key 8 (e.g., via the aperture, cavity or depression 17 thereof), to rotate the strut body 5 and the at least one threaded key 8 and cause adjustment of the axial/longitudinal arrangement between the strut body 5 and the corresponding threaded rod 12, 13 (via the threads of the at least one threaded key 8 and the corresponding threaded rod 12, 13). Manual axial and/or rotational adjustment of the outer sleeve 6 can thereby provide selective length adjustment of the strut assembly 110 (i.e., the axial X-X length between the joint of the threaded rod assembly 25 and the joint of the strut body 5, and thereby the distance and orientation between the first and second platforms 120, 130).

In some such embodiments, rotation of the outer sleeve 6 about the axis X-X when the at least one threaded key 8 is forced into engagement with the threaded rod assembly 25 via the camming surface of the outer sleeve 6 causes rotation of the strut body 5 and the at least one threaded key 8 about the threaded rod assembly 25 such that the threaded rod assembly 25 is axially translated through the strut body 5. In such embodiments, the joint 30 coupling the strut body 5 to the first platform 120 is configured to allow such rotation of the strut body 5 about the axis X-X.

In some embodiments, the outer sleeve 6 may be resiliently retained in a position such that the inner cam surface (s) thereof naturally or neutrally forces/maintains the at least one key 8 in engagement with the threaded rod assembly 25. For example, in some embodiments, the strut assembly 110 may include a spring 4 that naturally or neutrally resiliently maintains the outer sleeve 6 in an axial/longitudinal and/or rotational position on the end collar portion 7 of the strut body 5 such that the cam surface biases/forces the at least one pin 9 against the at least one key 8 such that the at least one key 8 is in engagement with the threaded rod assembly 25, as shown in FIGS. 9A-9C. In such embodiments, the strut assembly 110 may be configured such that the outer sleeve 6 can be axially translated along the axis X-X and/or rotationally translated about the axis X-X such that the inner camming surface thereof does not bias or force the at least one key 8 into engagement with the threaded rod assembly 25 (via the at least one pin 9) and allows the at least one key 8 to disengage with the threaded rod assembly 25. For example, the strut assembly 110 may include at least one biasing member 17 (e.g., at least one split ring or spring) that consistently/naturally biases the at least one key 8 radially away from the threaded rod assembly 25, as shown n FIGS. 9A-9C. In some embodiments, the strut assembly 110 may include a plurality of annularly/angularly arranged keys 8, and the at least one biasing member 17 may be positioned on an inside surface (e.g., interior groove) of the keys 8 such that the at least one biasing member 17 is elastically deformed when the outer sleeve 6 is in its naturally or neutrally biases position via the spring 4 such that the at least one biasing member 17 applies a preloaded radial force to the keys 8 that acts radially away from the threaded rod assembly 25. The outer sleeve 6 can thereby be rotated and/or radially translated (against the spring 4, for example) such that the cam surface(s) thereof no longer force the pin member 9 radially inward against the keys 8, and thereby allow the preload of the at least one biasing member 17 to force/radially translate the keys 8 away from (i.e., disengage) the threaded rod assembly 25. In such a configuration/arrangement of the outer sleeve 6, the axial length of the strut assembly 110 can be grossly adjusted by freely adjusting the relationship between the threaded rod assembly 25 and the strut body 5.

The threaded rod assembly 25 may be lengthened through the use of at least one add-on threaded rod 13 that includes external threads substantially the same as the external threads of the pre-existing component(s) of the threaded rod assemblies 25 (the first strut screw 12), and may otherwise be substantially similar to the pre-existing component(s) of the threaded rod assemblies 25. For example, the at least one add-on threaded rod 13 may include the same thread pitch as the external threads of the first strut screw 12 of the threaded rod assembly 25. The at least one add-on threaded rod 13 (and/or the pre-existing component of the threaded rod assemblies 25 forming the free end thereof—such as the first strut screw 12) may include an end configuration that ensures the clocking of the respective thread pitches such that the composite pitch remains continuous across the joined rods.

The threaded rod assembly 25 may be lengthened via the add-on threaded rod 13 via several methodologies. In one example (not shown), the threaded rods of the threaded rod assemblies 25 may include a cap screw arranged concentrically and placed within a central channel of the add-on threaded rod 13. The add-on threaded rod 13 can be configured such that the cap screw extends out the end of the add-on threaded rod 13, but the head of the cap screw is maintained or captured within the cavity. The existing first threaded rod 12 may include a concentric taped hole to threadably couple with the exposed portion of the cap screw. To accept an additional add-on threaded rod 13 to further lengthen the threaded rod assemblies 25, the pre-installed add-on threaded rod 13 may be configured to accept a threaded insert behind the captured cap screw within the cavity. The threaded insert may include the concentric taped hole for accepting the cap screw of the next add-on threaded rod 13. In such a manner, any number of add-on threaded rods 13 may be added to the threaded rod assemblies 25 in situ.

As another example, a threaded turnbuckle may be utilized as a connecting element between the in situ or pre-installed threaded rod (e.g., the first threaded rod 12 of a previously installed add-on threaded rod 13) and an add-on threaded rod 13. The threaded turnbuckle be configured to threadably engage with internal threads of central channels of the pre-installed threaded rod, such as the first threaded rod 12, and the add-on threaded rod 13. The turnbuckle may include a first portion with right hand sense external threads and a second portion with left hand sense external threads. The turnbuckle may also include a socket or another suitable driving feature incorporated into one end configured for providing a means of torque transmission to the turnbuckle. In such an embodiment, the internal threads of the in situ or pre-installed threaded rod can include a thread pitch whose sense was the same as the one on the opposite end of the driving feature of the turnbuckle, with the add-on threaded rod 13 having the same thread sense as the end of the turnbuckle having the driving feature. A drive element can be inserted down the central channel in the add-on threaded rod 13 and engaged with the driving feature of the turnbuckle. The add-on threaded rod 13, while on the shaft of the driving element and the driving feature of the turnbuckle engaged with the drive element, can be placed coaxial to the in situ or pre-installed threaded rod and the turnbuckle torqued to thread into both the in situ or pre-installed threaded rod and the add-on threaded rod 13 at the same time. Thread clocking of the external threads of the in situ or pre-installed threaded rod and the add-on threaded rod 13 may be achieved by inter digitation features at the mating ends of the in situ or pre-installed threaded rod and the add-on threaded rod 13.

As another example, the threaded rod assembly 25 may include a turnbuckle connecting element 22 that provides or allows for some means of pre-assembly such that the add-on threaded rod 13 and the connecting element 22 do not need to be separately handled during installation, as shown in FIGS. 9A-9C. Similar to the turnbuckle described above, the connecting element 22 may be configured to threadably engage with internal threads 58 of central channels of the pre-installed threaded rod, such as the first threaded rod 12, and the add-on threaded rod 13. The connecting element 22 may include a first portion 60 with external threads of a first pitch and a second portion 61 with external threads of a second pitch that is different than the first pitch. For example, the first pitch may be fine thread pitch and the second pitch may be a coarse thread pitch (or vice versa). While the pitch of the external threads of the first and second portions 60, 61 may differ, the sense of the threads may be same. As such, internal threads of the pre-installed threaded rod 12 may include the first pitch or the second pitch (and the corresponding thread sense) at least at a first end thereof, and the internal threads of the add-on threaded rod 13 may include the other of the first pitch or the second pitch (and the corresponding thread sense) at least at a first end thereof.

The internal threads of the second end of the add-on threaded rod 13 opposing the first end thereof may include the same thread pitch as the first end of the other of the first pitch or the second pitch. The second end of the add-on threaded rod 13 may thereby allow for an additional add-on threaded rod 13 to be installed to further lengthen the threaded rod assembly 25, and thereby further increase the length, and thereby range, of the threaded rod assembly 25 in situ.

In some embodiments, the internal threads of the pre-installed threaded rod 12 may include a coarse thread pitch, and the internal threads of the add-on threaded rod 13 may include a fine thread pitch (or vice versa). In such embodiments, if the connecting element 22 is torqued a first rotational direction and correspondingly threadably engaged with the internal threads of the pre-installed threaded rod 12 and the add-on threaded rod 13, the connecting element 22 progresses out of the add-on rod 13 at a given rate as it rotated, while it progresses into the pre-installed threaded rod 12 at a relatively faster rate—thus differentially bringing the add-on threaded rod 13 into contact with the pre-installed threaded rod 12. The connecting element 22 may include a socket or another suitable driving feature incorporated into one end configured for providing such torque transmission to the connecting element 22 (via through the channel of the pre-installed threaded rod 12, for example).

In this way, the connecting element 22 may be utilized to couple the add-on threaded rod 13 to the pre-installed threaded rod 12 without disconnecting or otherwise interfering with the pre-installed threaded rod 12 (i.e., can be installed in situ). In some embodiments, the connecting element 22 may be threaded into engagement with the add-on threaded rod 13, and the add-on threaded rod 13 may include finer pitched internal threads than the pre-installed threaded rod 12 (or vice versa). As shown in FIGS. 9A-9C, the connecting element 22 may include a non-threaded region 63 between the first and second portions 60, 61. The non-threaded region 63 may allow for the finer pitch threaded portion 60 or 61 of the connecting element 22 to initially be partially over-threaded into whichever of the add-on threaded rod 13 and the pre-installed threaded rod 12 includes the finer pitched internal threads.

As noted above, although two threaded rods 12,13 of an external bone fixation system are utilized to illustrate the exemplary use of one connecting element 22, a connecting element 22 may be utilized to bring together (or space apart) and couple any two rod members or portions (whether part of an external bone fixation system or part of another orthopedic or non-orthopedic mechanism or system). Further, although the connecting element 22 is depicted and described as having external threads 60, 61 and the first and second rod 12, 13 as having mating internal threads, the connecting element 22 may have internal threads and the members may have external threads.

Initially the second rod or member 13 and the connecting element 22 may be threadably coupled via relatively fine pitch threads and rotated or torqued together (e.g., via a tool) to threadably engage the first rod or member 12 via relatively course pitch threads. In such an embodiment, the non-threaded portion 63 of the connecting element 22 may extend between the first and second rods or members 12, 13. The second rod or member 13 and the connecting element 22 may be rotated together as a unit until the first and second rods or members 12, 13 meet such that relatively rotation between the first and second rods or members 12, 13 is prevented. The connecting element 22 may be further rotated therefrom such that the connecting element 22 travels axially through the first and second rods or members 12, 13. However, due to the finer pitch of the threaded connection between the connecting element 22 and the second rod or member 13 than the threaded connection between the connecting element 22 and the first rod or member 12, the connecting element 22 may travel slower or for a shorter distance as it is rotated through the second rod or member 13 than the first rod or member 12. In this way, the connecting element 22 may draw the first and second rods or members 12, 13 together, such as to an arrangement wherein the external threads of the first and second rods or members 12,13 are aligned or are continuous. It is noted that the combination of the relatively fine pitch threads and the relatively fine pitch threads of the connecting element 22 and the second rod member 12 and the first rod or member 12, respectively, provides for extremely high axial accuracy or adjustment between the first and second rods or members 12, 13 that may not be able to achieved via a single thread pitch due to physical restraints (i.e., a thread pitch equating to the difference in thread pitch between the fine and course thread pitches may not be realistically physically achievable).

In some embodiments, the connecting element 22 may be provided or otherwise pre-installed with the add-on threaded rod 13 before being coupled with the pre-installed threaded rod 12. To make the most efficient use of the engaged threads of the connecting element 22 within the add-on threaded rod 13, the add-on threaded rod 13 and/or the connecting element 22 may be configured such that the add-on threaded rod 13 and the connecting element 22 are rotated together as the connecting element 22 is threaded into the pre-installed threaded rod 12.

In some embodiments, at least the free end of the pre-installed threaded rod 12 and the ends of the add-on threaded rod 13 may include a keying element that ensures the correct timing between the external threads the pre-installed threaded rod 12 and the ends of the add-on threaded rod 13. In use, the first portion 60 of the connecting element 22 may be pre-installed within the channel of the add-on threaded rod 13, and the second portion 61 of the connecting element 22 may thereby extend from the add-on threaded rod 13. The add-on threaded rod 13 and the connecting element 22 may be torqued (e.g., rotated together as a unit) such that the second portion 61 of the connecting element 22 threadably engages the internal threads of the cavity of the pre-installed threaded rod 12, and thereby travel axially into the pre-installed threaded rod 12 and draw the add-on threaded rod 13 and the pre-installed threaded rod 12 together. The keying elements of the add-on threaded rod 13 and the pre-installed threaded rod 12 may be configured such that when mating faces thereof are within an optimal distance of one another, the mating faces of the keying elements contact one another and prevent relative rotation between the add-on threaded rod 13 and the pre-installed threaded rod 12.

In such an embodiment, the keying elements of the add-on threaded rod 13 and the pre-installed threaded rod 12 may include recesses corresponding to the mating faces that allow for relative axial translation between the add-on threaded rod 13 and the pre-installed threaded rod 12. In such a state, the driving feature of the connecting element 22 may be engaged via the channel of the add-on threaded rod 13 and rotated such that the connecting element 22 threadably translates through the cavities of the add-on threaded rod 13 and the pre-installed threaded rod 12 at different rates to thereby axial translate the add-on threaded rod 13 and the pre-installed threaded rod 12 towards one another. The connecting element 22 may be torqued until mating end faces of the add-on threaded rod 13 and the pre-installed threaded rod 12 contact each other. The add-on threaded rod 13 and the pre-installed threaded rod 12 may be configured such that when the mating end faces of the key elements of the add-on threaded rod 13 and the pre-installed threaded rod 12 are engaged, the add-on threaded rod 13 and the pre-installed threaded rod 12 are securely or rigidly coupled and the pitch of the external threads thereof are properly clocked.

In some embodiments, the free end of the pre-installed threaded rod 12 or the free end of add-on threaded rod 13, if installed, may include a guide bushing configured to mate with the keying elements, mating end faces and/or recesses thereof. The guide bushing may act to provide a relatively smooth surface for contact with the interior of the cavity of the strut body 5, and thereby protect the external threads thereof. A cap screw may be utilized to secure the guide bushing to the pre-installed threaded rod 12 or the free end of add-on threaded rod 13 if installed.

Although the connecting element 22 is described and utilized above with respect to a first pre-installed threaded rod 12 and a second add-on threaded rod 13 of the strut assembly 25, it is specifically and particularly contemplated herein that the connecting element 22 may be utilized with any other additional rod members.

As noted above and shown in FIGS. 1-7, 9A and 10-12, the strut body 5 of the strut assembly 110 may include a joint 30 that couples to the first platform 120 that provides for rotation and angulation of the strut body 5. The joint 30 between the strut body 5 and the first platform 120 is configured to allow the strut body 5 (and thereby the strut assembly 110 as a whole) to rotate or angle (roll, pitch, yaw and pose) with respect to all of the orthogonal axes translations (X, Y, Z position), including to rotate about the axis X-X. The joint 30 may allow rotation of the strut body 5 about the axis X-X with respect to the first platform 120 to, at least in part, allow rotation of the strut body 5 about the axis X-X (e.g., via the outer sleeve 6) to selectively lengthen or shorten the axial length of the strut assembly 110, as described above.

The first threaded rod 12 of the strut assembly 110 may also include a joint 31 that couples to the second platform 120 that provides for rotation and angulation of the threaded rod assembly 25 (whether just the first threaded rod 12 or the first threaded rod 12 and at least one second threaded rod 13 extending therefrom). The joint 31 between the first threaded rod 12 of the rod assembly 25 and the second platform 130 is configured to allow the first threaded rod 12 (and thereby the rod assembly 25 and the strut assembly 110 as a whole) to rotate or angle (roll, pitch, yaw and pose) with respect to all of the orthogonal axes translations (X, Y, Z position), including to rotate about the axis X-X. In some embodiments, the joint 31 may be of the same configuration as the joint 30. In some other embodiments, the configuration of the joint 31 differs from the configuration of the joint 30.

Figure 2:
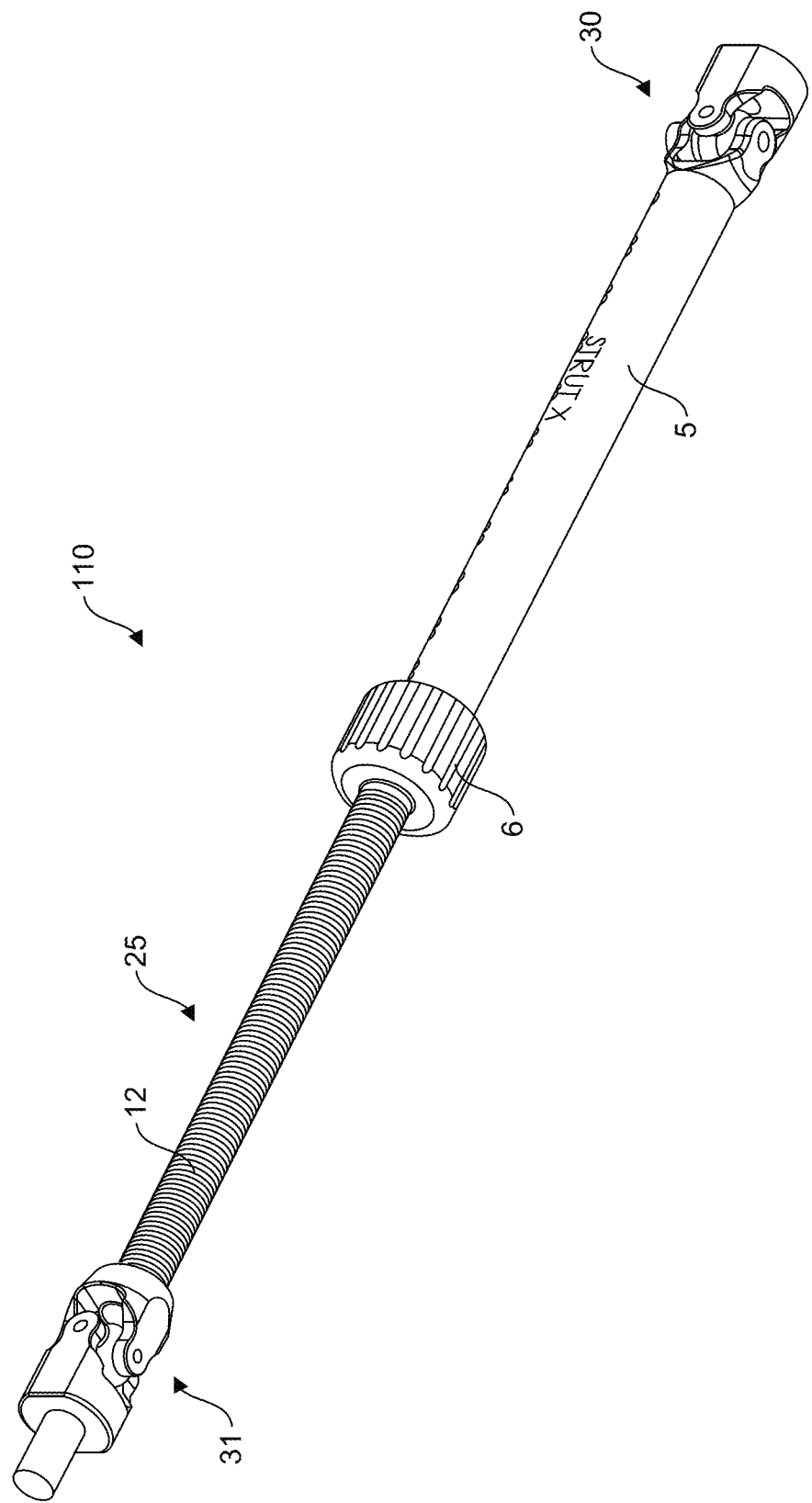
FIG. 2 illustrates another elevational perspective view of the strut assembly of FIG. 1.
Figure 3:
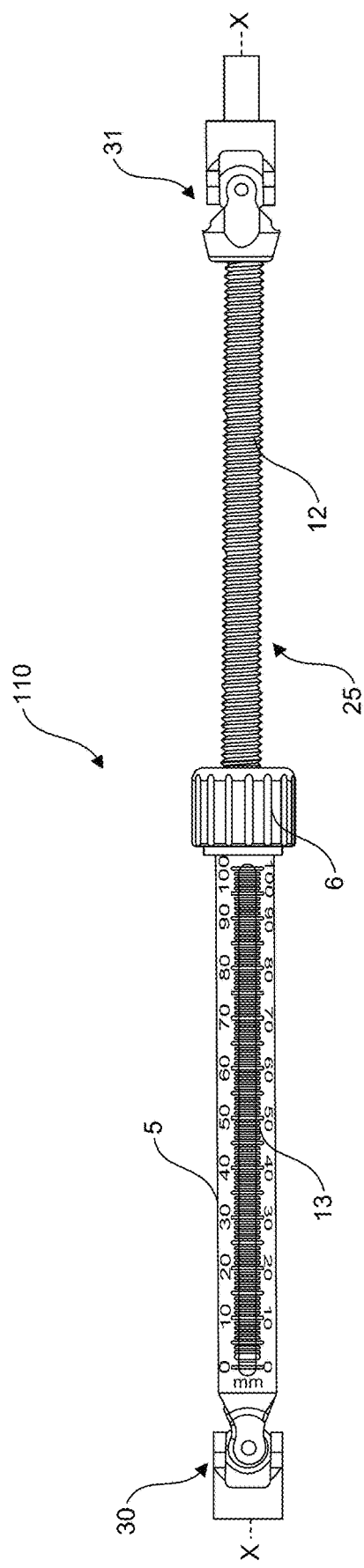
FIG. 3 illustrates a front view of the strut assembly of FIG. 1.
Figure 4:
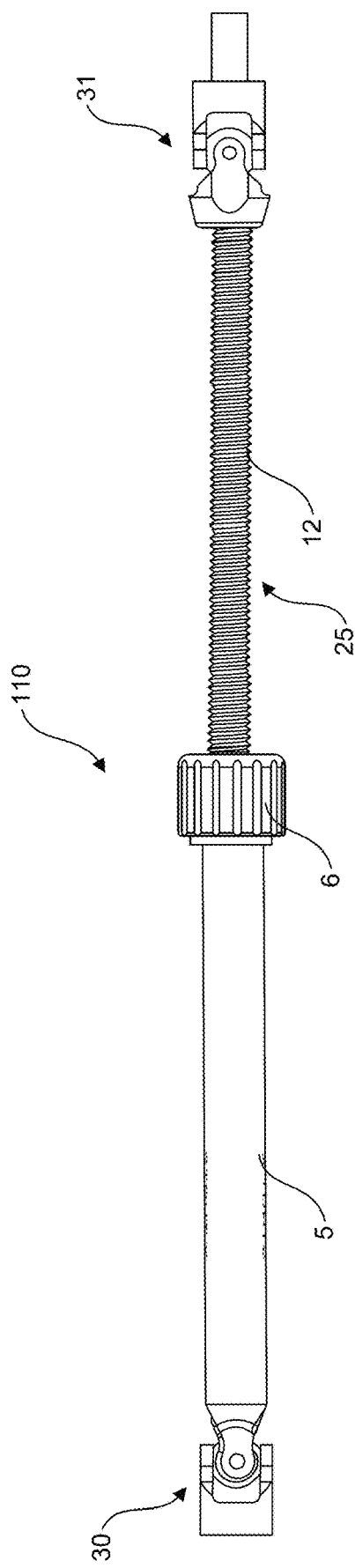
FIG. 4 illustrates a back side view of the strut assembly of FIG. 1.
Figure 5:
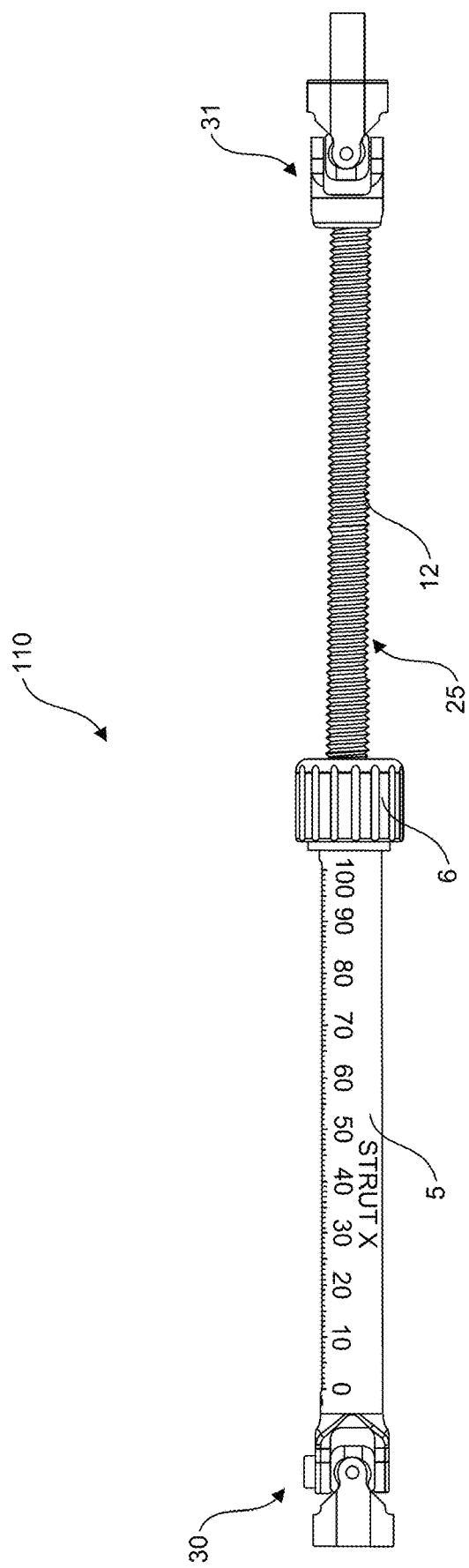
FIG. 5 illustrates a left side view of the strut assembly of FIG. 1.
Figure 6:
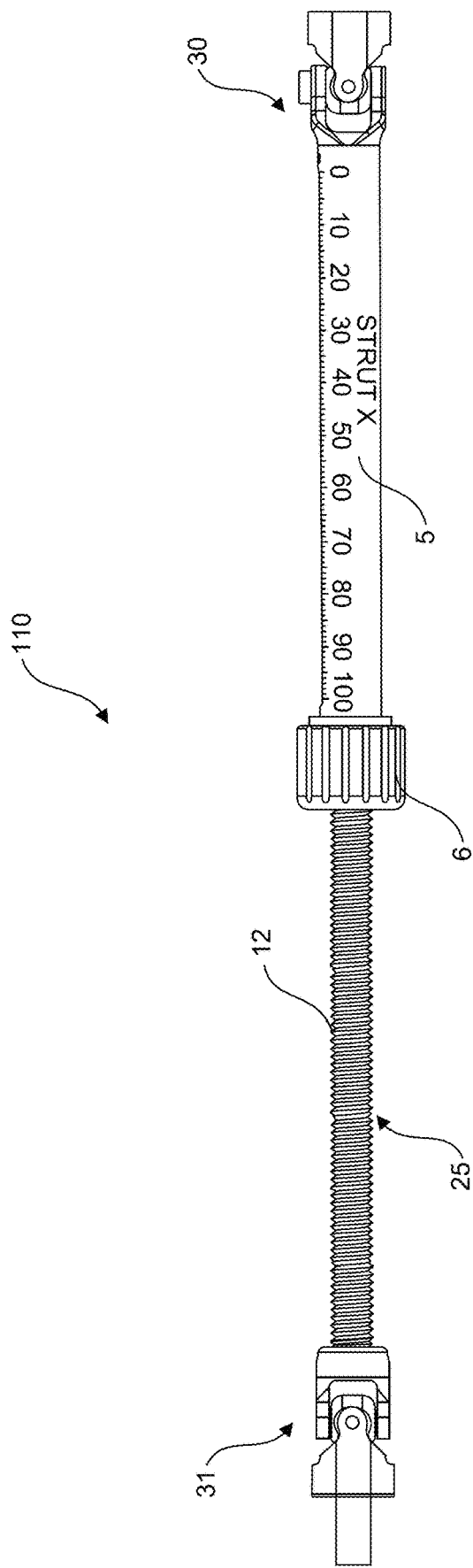
FIG. 6 illustrates a right side view of the strut assembly of FIG. 1.
Figure 7:
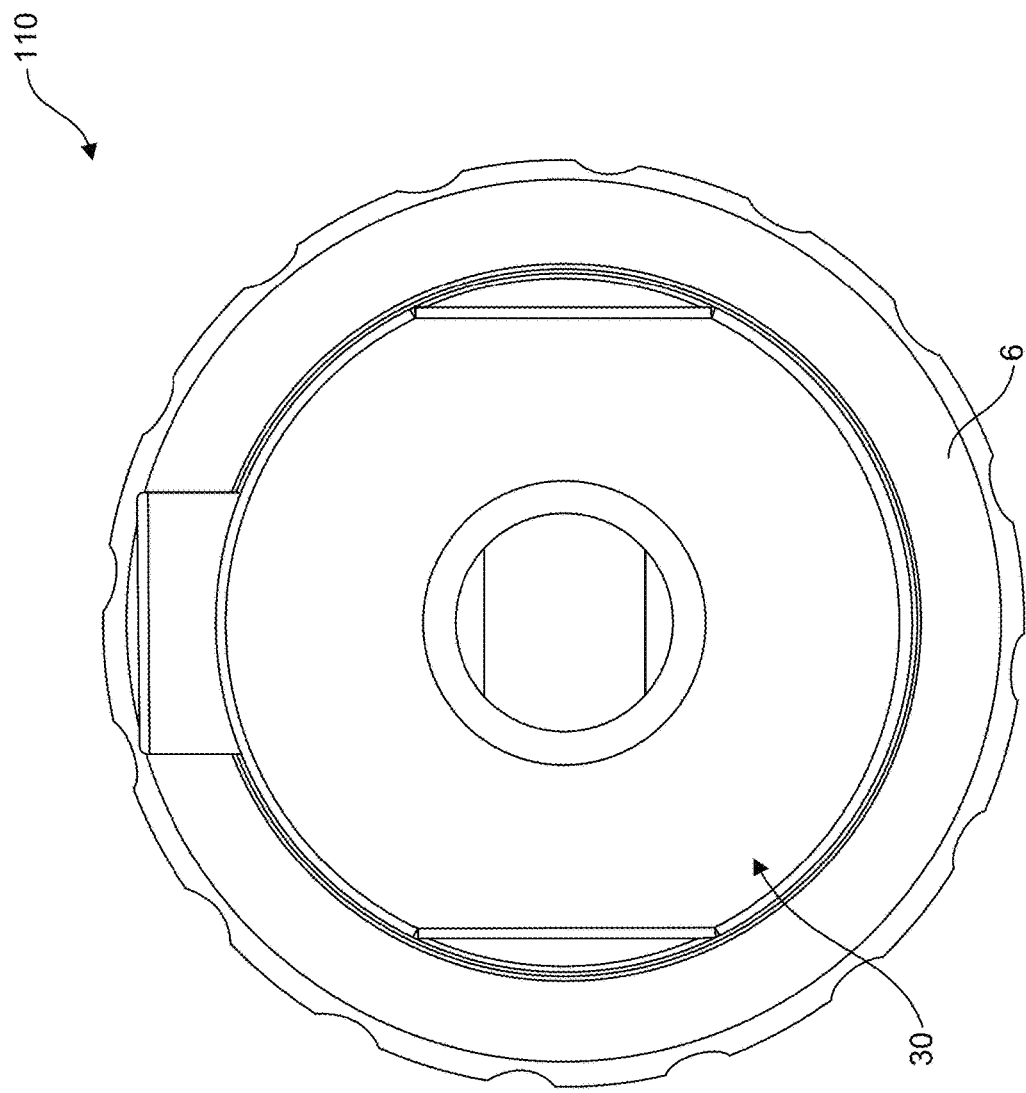
FIG. 7 illustrates a top view of the strut assembly of FIG. 1.
Figure 8:
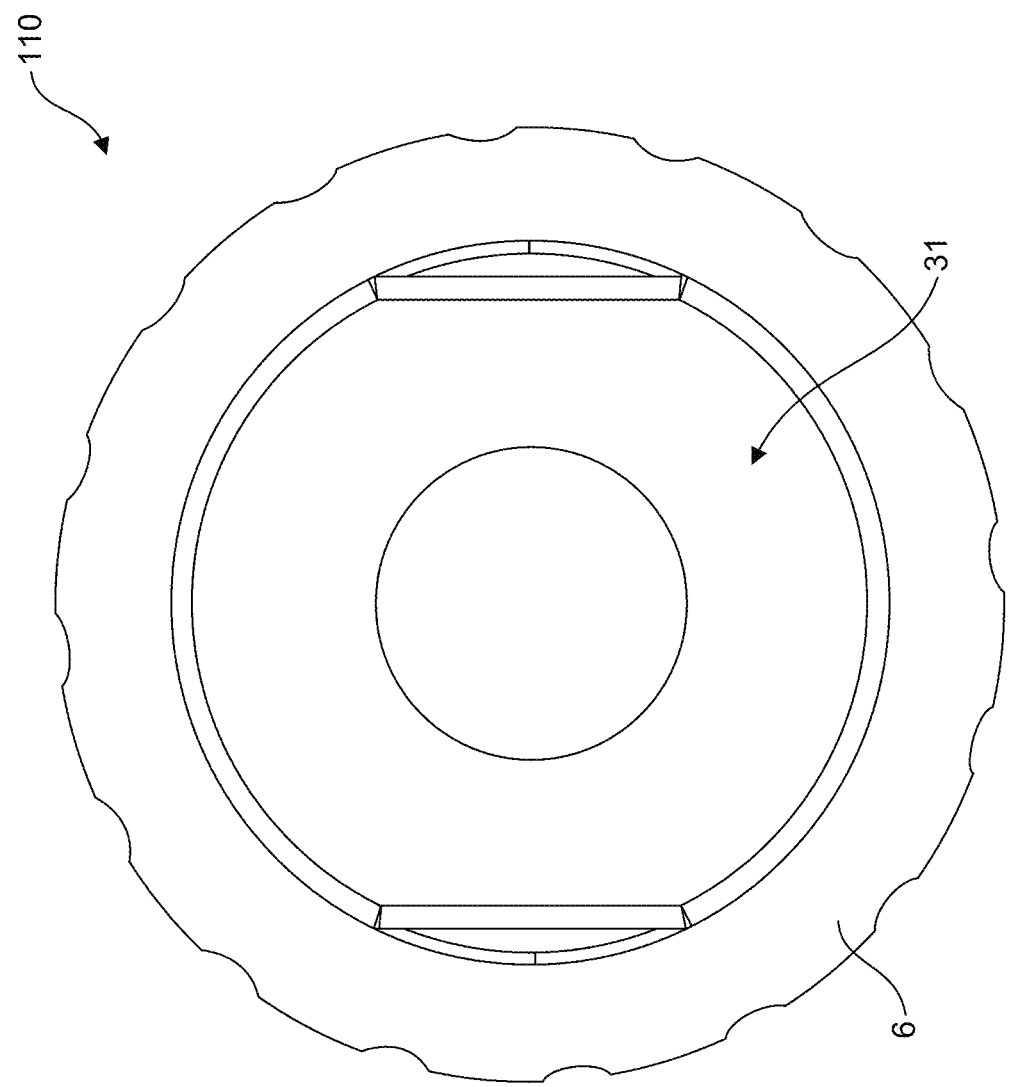
FIG. 8 illustrates a bottom view of the strut assembly of FIG. 1.

As shown in FIGS. 1-7, 9A and 10-12, the joint 30 that couples the strut body 5 of the strut assembly 110 to the first platform 120 may comprise a universal joint (i.e., a universal coupling, U-joint, Cardan joint, Spicer or Hardy Spicer joint, or Hooke's joint) that includes a first yoke portion, member or assembly that is rotatably coupled to the first platform 120, a second yoke portion, member or assembly that is coupled (rotatably or rigidly/fixedly coupled) to the strut body 5, and a cross mechanism or assembly that rotatably coupled between/to arm portions of the first and second yoke portions. As shown in FIGS. 2, 9A and 10, the first yoke portion or assembly may include an axially-extending aperture that extends from an axial end thereof. The axially-extending aperture may be configured to couple with a bolt, screw or like member that extends through an aperture of the first platform 120 and couples the first yoke portion of the joint 30 to the first platform 120, as shown in FIG. 10. In some other embodiments, the first yoke portion or assembly may include an axially-extending post that extends from an axial end thereof, as shown with the second joint 31 in FIGS. 1-6 and 8-10. The axially-extending post may be configured to extend through an aperture of the first platform 120 and couple the first yoke portion of the joint 30 to the first platform 120.

Figure 11:
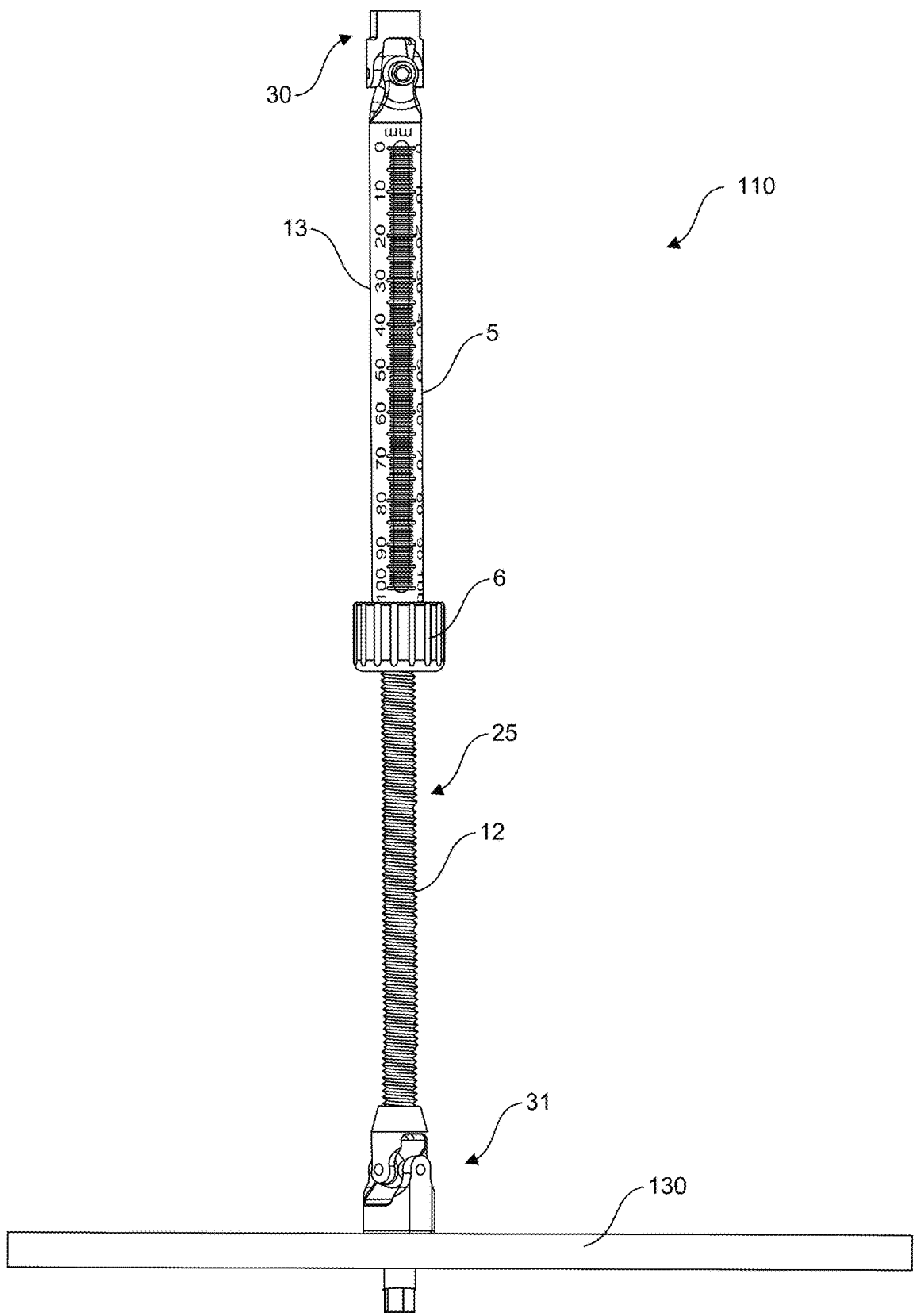
FIG. 11 illustrates a side view of a barrel end joint of the strut assembly of FIG. 10 disconnected from a respective platform.
Figure 12:
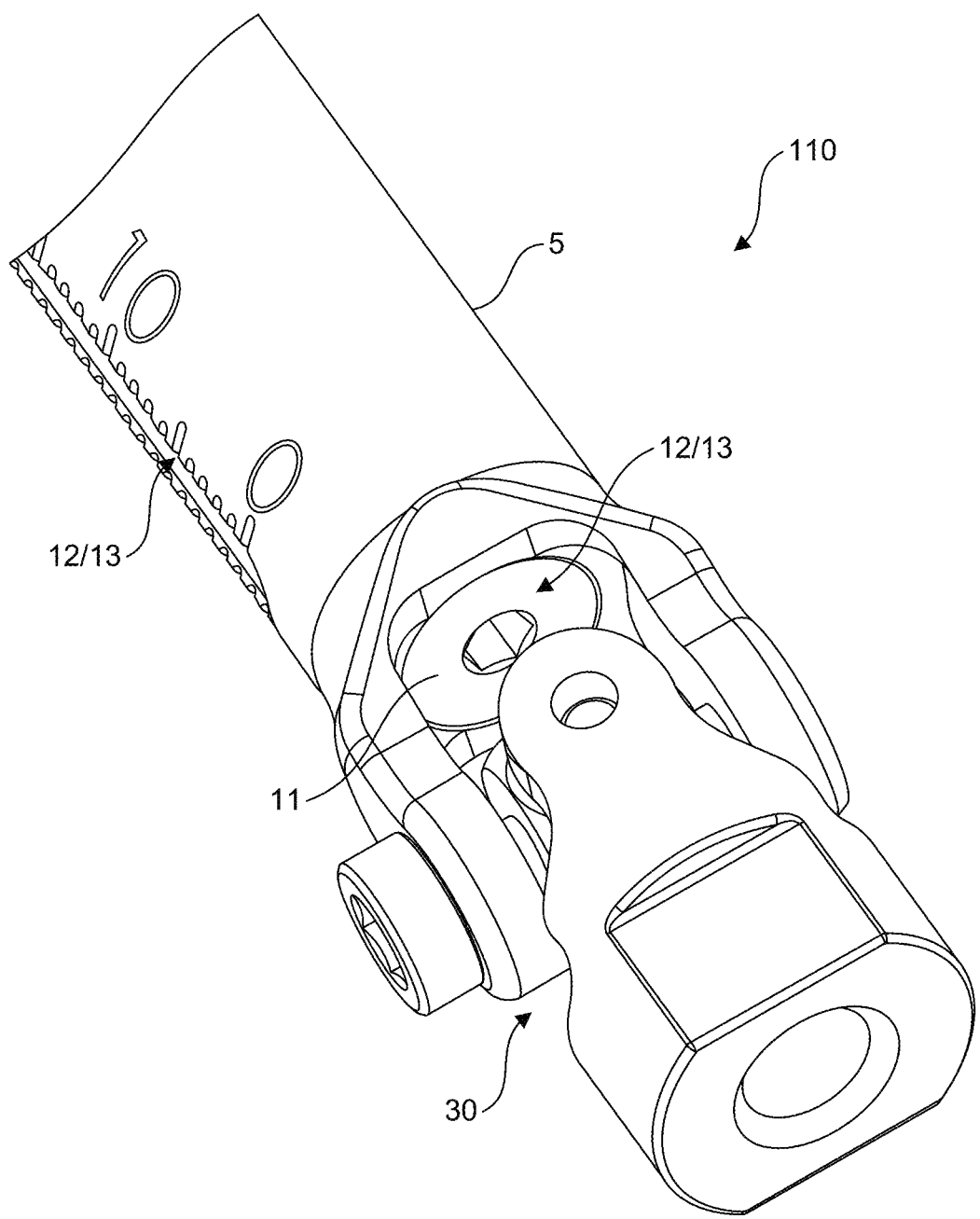
FIG. 12 illustrates a perspective view of the barrel end joint of the strut assembly of FIG. 11.

As shown in FIGS. 1-7, 9A and 10-12, the cross mechanism or assembly of the joint 30 may be configured to be disassembled or decoupled from at least the second yoke portion or assembly coupled to the strut body 5. For example, the portion of the cross mechanism extending between and rotatably coupled to the arms of the second yoke portion may be selectively removable (e.g., threadably removable) to separate or otherwise disassemble the cross mechanism and the first yoke (and thereby potentially the first platform 120) from the second yoke and the strut body 5 (and thereby the strut assembly 110 as a whole) without altering the length of the strut assembly 110, as shown in FIGS. 12 and 13.

In some embodiments, as shown in FIGS. 11 and 12, the joint 130 of the end of the strut barrel 5 may be detached or decoupled from the first platform 120 and the strut assembly 110 reoriented or angled and/or rotated (e.g., provided by movement of the joint 31 between the threaded rod assembly 25 and the second platform 130) such that the joint 130 is spaced from the first platform 120. The joint 130 may then be disassembled or decoupled to expose the inner cavity of the strut barrel 5 and the end of the threaded rod assembly 25 (i.e., an end of the first threaded rod 12 or the "last" second threaded rod 13 (if included)), as shown in FIG. 13. Alternatively, the joint 130 may be disassembled or decoupled to detached or decouple the strut barrel 5 from the first platform 120 (and the joke of the joint 30 coupled thereto), and the strut assembly 110 reoriented or angled and/or rotated (e.g., provided by movement of the joint 31 between the threaded rod assembly 25 and the second platform 130) such that the end of the strut barrel 5 with the second yoke portion of the joint 130 is spaced from the first platform 120 and the inner cavity of the strut barrel 5 and the end of the threaded rod assembly 25 are exposed, as shown in FIG. 13.

Figure 13:
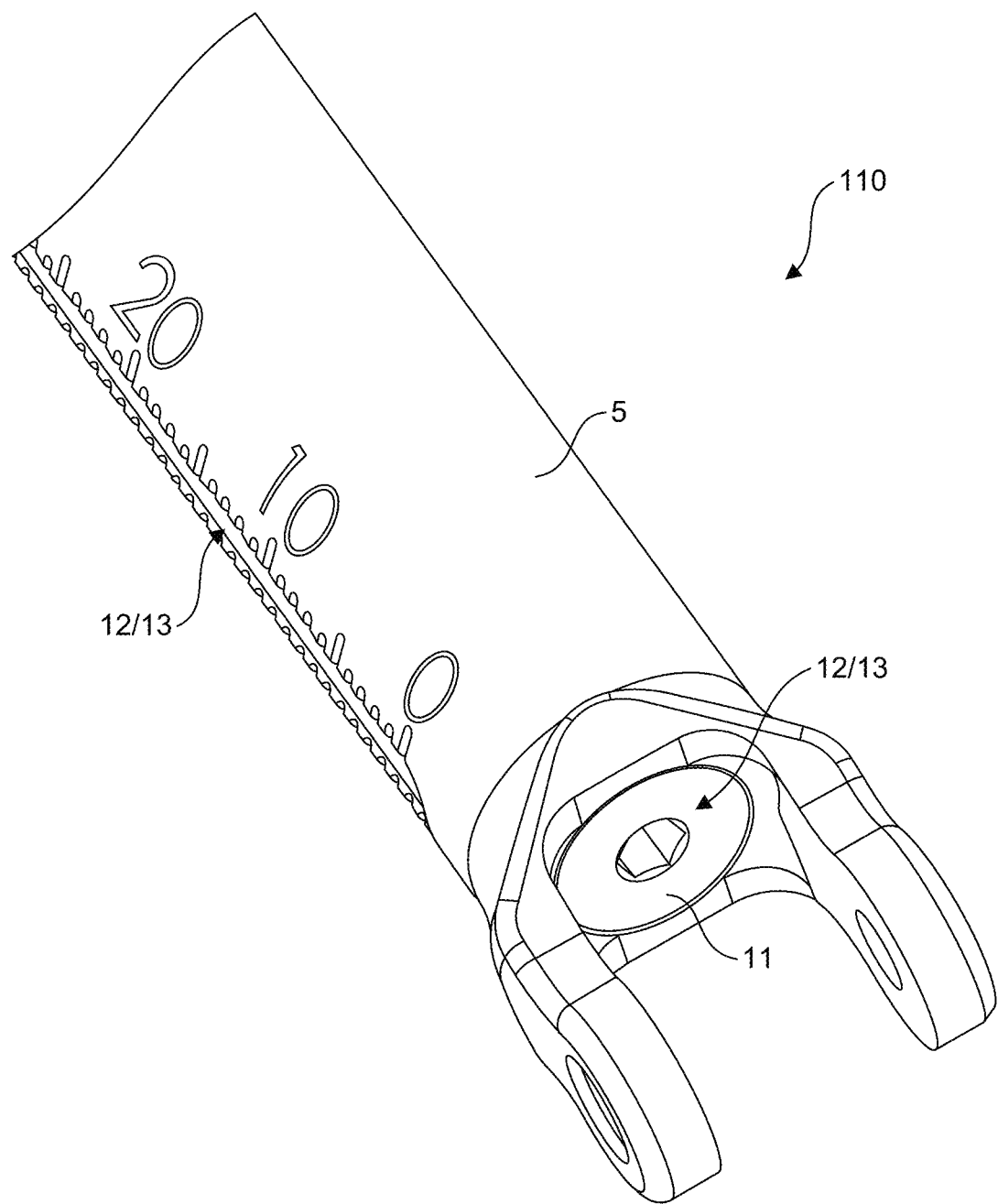
FIG. 13 illustrates a perspective view of a barrel end of the strut assembly of FIG. 12 with components of the barrel end joint removed and a threaded rod of the strut assembly being exposed.
Figure 14:
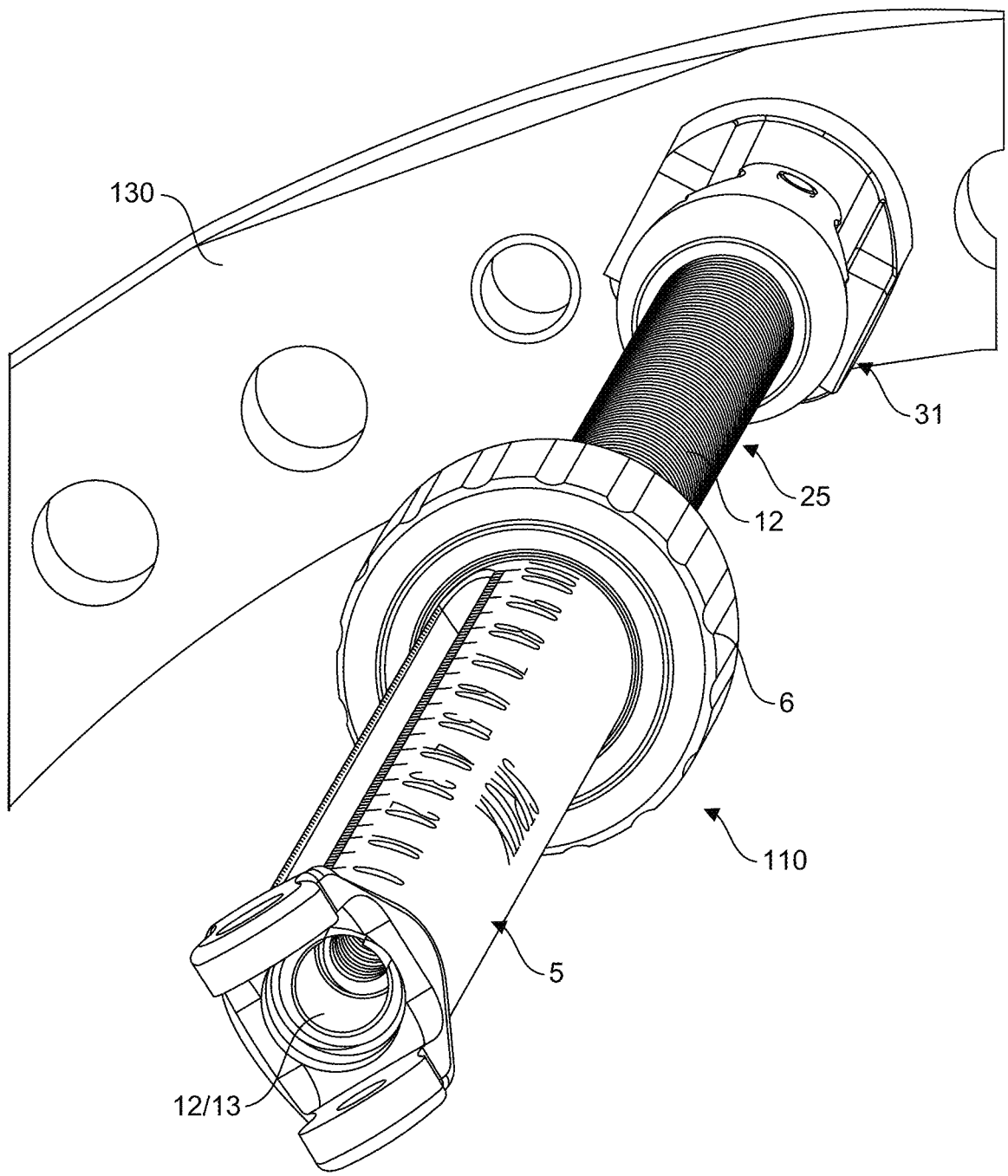
FIG. 14 illustrates a perspective view of the barrel end of the strut assembly of FIG. 13 with a cap member removed from an end of the threaded rod and an internal cavity of the threaded rod being exposed.

As shown in FIG. 13, in some embodiments, the end of the end of the threaded rod assembly 25 (i.e., an end of the first threaded rod 12 or the "last" second add-on threaded rod 13 (if included)) may include a cap member 11 that couples (e.g., threadably couples) within the end of the threaded rod assembly 25 and extends over or otherwise prevent access to the threaded internal cavity of the threaded rod assembly 25 (i.e., the first threaded rod 12 or the "last" second add-on threaded rod 13, if included) and the end of the threaded rod assembly 25 (e.g., the key element thereof). In such embodiments, the cap member 11 may be removed (e.g., threadably removed) from the end of the threaded rod assembly 25 to expose the internal threaded aperture and end of the threaded rod assembly 25, as shown in FIG. 14.

With the internal threaded aperture and end of the threaded rod assembly 25 exposed, an add-on threaded rod 13 may be coupled to the end of the threaded rod assembly 25 (i.e., the first threaded rod 12 or the "last" second add-on threaded rod 13, if included) via the connecting element 22 to increase the total length of the threaded rod assembly 12, and thereby the total potential axial length adjustability or travel afforded by the strut assembly 110. Similarly, with the internal threaded aperture and end of the threaded rod assembly 25 exposed, a "last" add-on threaded rod 13 may be decoupled or removed from the end of the threaded rod assembly 25 (i.e., from the first threaded rod 12 or a "second-to-last" second add-on threaded rod 13, if included) via removal of the connecting element 22 (e.g., via the internal cavity of the "last" add-on second threaded rod 13 and a driver) to decrease or shorten the total length of the threaded rod assembly 12, and thereby the total potential axial length adjustability or travel afforded by the strut assembly 110.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A length-adjustable strut assembly comprising:
   an externally threaded rod portion including a first externally threaded rod member;
   a strut barrel assembly including a strut barrel portion with an internal cavity and an adjustment portion, the rod portion extending within the internal cavity of the strut barrel portion and selectively threadably coupled with at least one key of the adjustment portion;
   a first joint assembly at an end of the first externally threaded rod member, the first joint assembly configured to removably couple to a first platform and allow angulation and rotation between the first externally threaded rod member and the first platform;
   a second joint assembly at an end of the strut barrel portion, the second joint assembly configured to removably couple to a second platform and allow angulation and rotation between the strut barrel assembly and the second platform, and
   wherein at least one portion of the second joint is configured to be selectively disassembled from the end of the strut barrel portion to expose the internal cavity of the strut barrel portion and an end of the rod portion,
   wherein selective rotation of the adjustment portion rotates the strut barrel portion, and wherein rotation of the strut barrel portion rotates the at least one key about the rod portion to thereby adjust an axial length of the strut assembly between the first and second joint assemblies.

2. The strut assembly of claim 1, wherein the second joint assembly comprises a universal joint.

3. The strut assembly of claim 2, wherein the universal joint comprises a first yoke portion configured to be couple to the first platform, a second yoke portion at the end of the strut barrel portion, and a cross assembly rotatably coupled with the first and second yoke portions.

4. The strut assembly of claim 3, wherein the cross assembly is configured to be selectively disassembled from the second yoke portion.

5. The strut assembly of claim 4, wherein the cross assembly is coupled to the second yoke portion via a first removable pin portion of the cross assembly.

6. The strut assembly of claim 5, wherein the first removable pin portion extends between a pair of spaced arm portions of the second yoke portion and is coupled to a second pin portion of the cross assembly.

7. The strut assembly of claim 6, wherein the second pin portion extends between a pair of spaced arm portions of the first yoke portion.

8. The strut assembly of claim 7, wherein the first removable pin portion and the second pin portion are coupled together via a universal joint block.

9. The strut assembly of claim 8, wherein the first removable pin portion comprises a pin extending through a through hole of the universal joint block.

10. The strut assembly of claim 9, wherein the second pin portion comprises a pair of pin members extending within a pair of corresponding apertures of the universal joint block.

11. The strut assembly of claim 1, wherein the end of the rod portion includes an internally threaded internal axial aperture.

12. The strut assembly of claim 1, wherein the rod portion includes a second externally threaded rod member coaxially coupled to an end portion of the first externally threaded rod member.

13. A length-adjustable strut assembly, comprising:
an externally threaded rod portion including a first externally threaded rod member;
a strut barrel assembly including a strut barrel portion with an internal cavity and an adjustment portion, the rod portion extending within the internal cavity of the strut barrel portion and selectively threadably coupled with at least one key of the adjustment portion;
a first joint assembly at an end of the first externally threaded rod member, the first joint assembly configured to removably couple to a first platform and allow angulation and rotation between the first externally threaded rod member and the first platform;
a second joint assembly at an end of the strut barrel portion, the second joint assembly configured to removably couple to a second platform and allow angulation and rotation between the strut barrel assembly and the second platform, and
wherein at least one portion of the second joint is configured to be selectively disassembled from the end of the strut barrel portion to expose the internal cavity of the strut barrel portion and an end of the rod portion, wherein the rod portion includes a second externally threaded rod member coaxially coupled to an end portion of the first externally threaded rod member,
wherein the first externally threaded rod member and the second externally threaded rod member include external threads that form a continuous external thread profile.

14. The strut assembly of claim 13, wherein the first externally threaded rod member and the second externally threaded rod member are coupled via a connecting member, and wherein a first portion of the connecting member is threadably coupled within a first internally threaded internal axial aperture of the first externally threaded rod member and a second portion of the connecting member is threadably coupled within a second internally threaded internal axial aperture of the second externally threaded rod member.

15. The strut assembly of claim 14, wherein the first portion of the connecting member and the first internally threaded internal axial aperture of the first externally threaded rod member include threads of a first pitch, and wherein the second portion of the connecting member and the second internally threaded internal axial aperture of the second externally threaded rod member include threads of a second pitch that differs from the first pitch.

16. The strut assembly of claim 1, wherein selective rotation of at least one of the adjustment portion and the strut barrel portion rotates the at least one key about the rod portion, and thereby adjusts an axial length of the strut assembly between the first and second joints.

17. The strut assembly of claim 1, wherein the adjustment portion further comprises a sleeve member movably coupled over an end collar portion of the strut barrel portion, and at least one pin member extending through a corresponding aperture in the end collar portion.

18. The strut assembly of claim 17, wherein a first end portion of the at least one pin member engages a back side of the at least one key and a second end portion of the at least one pin member engages an interior surface of the sleeve member.

19. The strut assembly of claim 18, wherein the back side of the at least one key includes a depression, the second end portion of the at least one pin member being positioned within the depression.

20. The strut assembly of claim 18, wherein the interior surface of the sleeve member includes at least one first portion configured as a cam surface that radially positions the at least one pin member such that the at least one pin member positions the at least one key in threaded engagement with the externally threaded rod portion.

21. The strut assembly of claim 20, wherein, when the at least one pin member is engaged with the at least one first portion of the interior surface of the sleeve member, rotation of the sleeve member effectuates rotation of the at least one pin member, the at least one key and the strut barrel portion.

22. The strut assembly of claim 20, wherein the interior surface of the sleeve member includes at least one second portion configured as a relief surface that radially positions the at least one pin member such that the at least one pin member decouples the at least one key from the externally threaded rod portion.

23. The strut assembly of claim 22, wherein the adjustment portion further comprises at least one biasing member that naturally biases the at least one key radially away from the externally threaded rod portion.

24. The strut assembly of claim 22, wherein the at least one first portion and the at least one second portion of the interior surface of the sleeve member are at least one of axially and angularly spaced.

25. The strut assembly of claim 24, wherein the adjustment portion further comprises at least one spring member that biases the sleeve member in at least one of an axial and angular arrangement with respect to the strut barrel portion such that the sleeve member is normally biased into a position with the at least one pin member engaged with the at least one first portion of the interior surface of the sleeve member.

26. An external bone fixation system, comprising:
- a first platform defining an opening and configured to couple to a first anatomical structure;
- a second platform defining an opening and configured to couple to a second anatomical structure; and
- at least one length-adjustable strut assembly comprising:
  - an externally threaded rod portion including a first externally threaded rod member;
  - a strut barrel assembly including a strut barrel portion with an internal cavity and an adjustment portion, the rod portion extending within the internal cavity of the strut barrel portion and selectively threadably coupled with at least one key of the adjustment portion;
  - a first joint assembly at an end of the first externally threaded rod member, the first joint assembly configured to removably couple to a first platform and allow angulation and rotation between the first externally threaded rod member and the first platform;
  - a second joint assembly at an end of the strut barrel portion, the second joint assembly configured to removably couple to a second platform and allow angulation and rotation between the strut barrel assembly and the second platform, and wherein at least one portion of the second joint is configured to be selectively disassembled from the end of the strut barrel portion to expose the internal cavity of the strut barrel portion and an end of the rod portion, wherein selective rotation of the adjustment portion rotates the strut barrel portion, and wherein rotation of the strut barrel portion rotates the at least one key about the rod portion to thereby adjust an axial length of the strut assembly between the first and second joint assemblies.

* * * * *